(12) United States Patent
Shiga

(10) Patent No.: US 7,811,519 B2
(45) Date of Patent: Oct. 12, 2010

(54) ANALYSIS DEVICE, ANALYSIS DISK, AND ANALYSIS SYSTEM USING THE DEVICE AND THE DISK

(75) Inventor: Takashi Shiga, Ehime (JP)

(73) Assignee: Panasonic Corporation, Osaka (JP)

( * ) Notice: Subject to any disclaimer, the term of this patent is extended or adjusted under 35 U.S.C. 154(b) by 927 days.

(21) Appl. No.: 11/572,173

(22) PCT Filed: Jul. 19, 2005

(86) PCT No.: PCT/JP2005/013254

§ 371 (c)(1),
(2), (4) Date: Jan. 16, 2007

(87) PCT Pub. No.: WO2006/011393

PCT Pub. Date: Feb. 2, 2006

(65) Prior Publication Data

US 2008/0019875 A1    Jan. 24, 2008

(30) Foreign Application Priority Data

Jul. 29, 2004 (JP) ............................. 2004-221350

(51) Int. Cl.
*G01F 3/06* (2006.01)
(52) U.S. Cl. .................... 422/72; 422/68.1; 422/99; 422/100
(58) Field of Classification Search .................. 422/72, 422/57, 68.1, 99, 100
See application file for complete search history.

(56) References Cited

U.S. PATENT DOCUMENTS

2001/0055812 A1* 12/2001 Mian et al. .................... 422/72

FOREIGN PATENT DOCUMENTS

| JP | 03-225276 | 10/1991 |
|----|-----------|---------|
| JP | 03-225278 | 10/1991 |
| JP | 06-043158 | 2/1994 |
| JP | 10-504397 | 4/1998 |
| JP | 2003-270128 | 9/2003 |

OTHER PUBLICATIONS

International Search Report for corresponding PCT International Application No. PCT/JP2005/013254 dated Oct. 25, 2005.

* cited by examiner

*Primary Examiner*—Jill Warden
*Assistant Examiner*—Sharon Pregler
(74) *Attorney, Agent, or Firm*—RatnerPrestia

(57) ABSTRACT

An analysis system includes an analyzing disk, and an analyzer. The analyzing disk includes a chamber into which a test sample is input. The test sample includes a first component and a second component. The analyzer includes a driving unit for rotating the analyzing disk so as to centrifuge the first component and the second component of the test sample from each other in the first chamber, an optical unit movable in a radial direction of the analyzing disk for illuminating light to the analyzing disk and detecting light from the test sample in the first chamber, and a controller for detecting, based on the light from the optical unit, a boundary between the first component and the second component centrifuged in the first chamber. This analysis system monitors the status of the separation due to the centrifugation, hence analyzing the test sample accurately.

12 Claims, 9 Drawing Sheets

7,811,519 B2

ANALYSIS DEVICE, ANALYSIS DISK, AND ANALYSIS SYSTEM USING THE DEVICE AND THE DISK

This Application is a U.S. National Phase Application of PCT International Application No. PCT/JP2005/013254.

TECHNICAL FIELD

The present invention relates to an analyzer that centrifuges test sample, such as blood, and analyzes a specific component of the centrifuged sample, to an analyzing disk used for the analyzer, and to an analysis system including the analyzer and the disk.

BACKGROUND ART

Japanese Patent Laid-Open Publication No.10-504397 discloses a conventional analyzer that uses an optical disc, such as a compact disc to record audio or video data thereon, and an optical disc drive for reproducing the data to analyze a specific component of a test sample by tracing tracks on the optical disc with the test sample arranged thereon.

FIG. 8 is a top view of analyzing disk 1100 used for a conventional analyzer. Disk 1100 is formed according to the standard of a conventional optical disc for recording audio or video data thereon and is provided with track 1101 which has address data and is formed with pits and grooves.

Analyzing disk 1100 includes centrifuge chamber 1102, measuring chamber 1103, overflow chamber 1105, and analysis chamber 1104 which are provided thereon. Centrifuge chamber 1102 has inlet 1108 through which a test sample, such as blood, is input, and the input test sample is centrifuged in the chamber. Measuring chamber 1103 collects a predetermined amount of the centrifuged test sample. Overflow chamber 1105 stores the rest of the test sample other than the sample collected in measuring chamber 1103. Analysis chamber 1104 analyzes the test sample supplied from measuring chamber 1103. These chambers are connected with each other with capillary tube 1109, a minute duct. Analysis chamber 1104 can store a reagent, for example, for examining a color reaction with the test sample.

Japanese Patent Laid-Open Publication No.2003-270128 discloses that the position of each chamber can be specified by the analyzer based on the positional relationship of each chamber with trigger patterns 1106 and 1107. Trigger patterns 1106 and 1107 are provided on an outer circumferential edge of analyzing disk 1100 by printing or the like. Trigger pattern 1106 is used to specify the position of centrifuge chamber 1102, and trigger pattern 1107 is used to specify the positions of measuring chamber 1103 and analysis chamber 1104.

Analyzing disk 1100 includes four sets each having the chambers and the trigger patterns arranged on the circumference separated from each other. Analyzing disk 1100 is produced by bonding a substrate with the chambers thereon onto a disk having the track with the address data recorded thereon.

FIG. 9 is a block diagram of a conventional analyzer using analyzing disk 1100. The analyzer has a structure of a conventional optical disc drive. More specifically, the apparatus includes optical pickup 1020 for illuminating disk 1100 with laser, traverse motor 1021 for moving optical pickup 1020, spindle motor 1022 for rotating disk 1100, servocontrol circuit 1024 for controlling these components, signal processing circuit 1025 for converting a signal from optical pickup 1020 into data, and controller 1023 for controlling these circuits. Photodetector 1011 detects laser emitted from optical pickup 1020 and transmitted through disk 1100. A signal corresponding to the detected laser is converted into digital data by analog/digital (A/D) converter 1013. The digital data is processed by signal processing circuit 1014 and is stored in RAM 1016. Controller 1015 controls signal processing circuit 1014 and RAM 1016. Photosensor 1017 detects trigger patterns 1106 and 1107 provided on disk 1100.

An operation of analyzing disk 1100 and the analyzer treating blood as the test sample. The blood, the test sample is input through inlet 1108 of analyzing disk 1100. Analyzing disk 1100 is into the analyzer. The analyzer executes spin-up processes including disk discrimination, focus adjustment, and tracking adjustment, to prepare for tracing track 1101 provided on analyzing disk 1100.

First, centrifugation is executed to separate a target component from the others in the test sample. The blood, the test sample, exists in centrifuge chamber 1102 of analyzing disk 1100 and is centrifuged into a blood cell component and a plasma component while analyzing disk 1100 rotates at a predetermined rotation speed for a predetermined time. The plasma component is used to monitor the level of cholesterol and glucose.

After the centrifugation completes, analyzing disk 1100 stops its rotation. When analyzing disk 1100 stops, the blood plasma to be tested which is separated in centrifuge chamber 1102 at the inner circumference side of the disk is transferred and collected into measuring chamber 1103 through capillary tube 1109 due to capillarity. Analyzing disk 1100 rotates again at a predetermined rotation speed for a predetermined time in order to measure the collected blood plasma component, and then, the rotation of analyzing disk 1100 is stopped. When the rotation is stopped, the blood plasma component to be tested starts to be transferred from measuring chamber 1103 to analysis chamber 1104. Then, disk 1103 starts rotating again, and the entire target blood plasma component reacts with a reagent input in analysis chamber 1104.

After these processes complete, optical pickup 1020 moves to the radial position of analysis chamber 1104, and starts tracing track 1101 of analyzing disk 1100 at the position. Then, trigger pattern 1107 provided on analyzing disk 1100 is detected by photosensor 1017. Light transmitting from optical pickup 1020 through analysis chamber 1104 is detected by photodetector 1011 for a predetermined time after trigger pattern 1107 is detected by photosensor 1017. A signal corresponding to the detected light is converted to digital data by A/D converter 1013, and the data is stored in RAM 1016. The level of cholesterol, glucose, and the like in the blood plasma component to be tested is monitored bade on the stored data, and an analysis result is provided.

In the conventional analyzer, it is not confirmed, during or after the centrifugation, whether a target component and the other component, i.e., the blood plasma component and a cell component, are separated from each other in centrifuge chamber 1102. If they are not separated appropriately, a component interfering with analysis which is to be separated ordinarily flows into measuring chamber 1103 and analysis chamber 1104. If the plasma component and the cell component of blood is not centrifuged completely, capillary tube 1109 connecting centrifuge chamber 1102 with measuring chamber 1103 may be clogged with the cell component. In this case, the predetermined amount of the plasma component is not collected in measuring chamber 1103, accordingly preventing the plasma component from being analyzed accurately.

SUMMARY OF THE INVENTION

An analysis system includes an analyzing disk, and an analyzer. The analyzing disk includes a chamber into which a test sample is input. The test sample includes a first component and a second component. The analyzer includes a driving unit for rotating the analyzing disk so as to centrifuge the first component and the second component of the test sample from each other in the first chamber, an optical unit movable in a radial direction of the analyzing disk for illuminating light to the analyzing disk and detecting light from the test sample in the first chamber, and a controller for detecting, based on the light from the optical unit, a boundary between the first component and the second component centrifuged in the first chamber.

This analysis system monitors the status of the separation due to the centrifugation, hence analyzing the test sample accurately.

REFERENCE MARKS IN THE DRAWINGS

11 Photodetector
15 Controller
15A Controller
17 Photosensor
20 Optical Pickup
21 Traverse Motor
22 Driving Unit
30 Position-Detecting Switch
100 Analyzing Disk
101 Track
102 Centrifuge Chamber (First Chamber)
103 Measuring Chamber
104 Analysis Chamber (Second Chamber)
105 Overflow Chamber
106 Trigger Pattern
107 Trigger Pattern
108 Inlet
109A Capillary Tube
109B Capillary Tube
109C Capillary Tube
110 Bar Code
200 Blood (Test Sample)
201 Blood Plasma Component (First Component)
202 Blood Cell Component (Second Component)
203 Trace Direction
210 Marking
300 Analyzer
400 Analyzing Disk
500 Analyzing Disk
600 Analyzer

DETAILED DESCRIPTION OF PREFERRED EMBODIMENTS

Exemplary Embodiment 1

Figure 1:
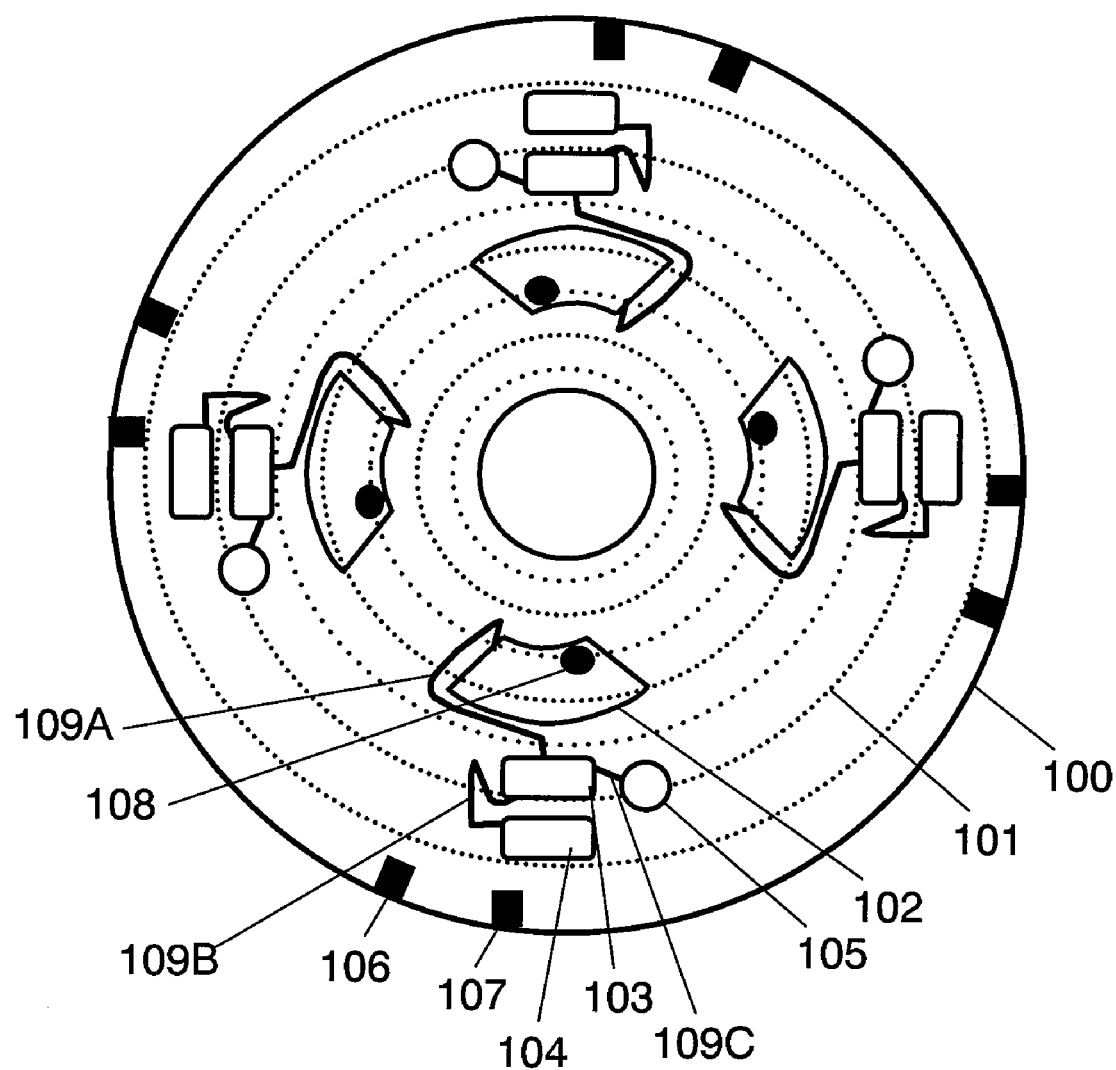
FIG. 1 is a top view of an analyzing disk according to Exemplary Embodiment 1 of the present invention.

FIG. 1 is a top view of analyzing disk 100 according to Exemplary Embodiment 1 of the present invention.

Disk 100 is formed according to the standard of a conventional optical disc for recording audio or video data. Disk 100 has track 101 which has address data and is formed with pits and grooves.

Analyzing disk 100 includes centrifuge chamber 102, measuring chamber 103, overflow chamber 105, and analysis chamber 104 which are provided thereon. Centrifuge chamber 102 has inlet 108 through which a test sample, such as blood, is input, and the input test sample is centrifuged in the chamber. Measuring chamber 103 collects a predetermined amount of the centrifuged test sample. Overflow chamber 105 stores the rest of the test sample other than the sample collected in measuring chamber 103. Analysis chamber 104 analyzes the test sample supplied from measuring chamber 103. These chambers are connected with each other through capillary tubes 109A, 109B, and 109C, minute ducts. Analysis chamber 104 can store a reagent, for example, for examining a color reaction with the test sample.

The position of each chamber can be specified by an analyzer based on the positional relationship with trigger patterns 106 and 107. Trigger patterns 106 and 107 are formed on an outer circumferential edge of analyzing disk 100 by printing or the like. Trigger pattern 106 is used to specify the position of centrifuge chamber 102, and trigger pattern 107 is used to specify the positions of measuring chamber 103 and analysis chamber 104.

Analyzing disk 100 includes four sets each including the chambers and trigger patterns separately on its circumference. Analyzing disk 100 is produced by bonding a substrate having the chambers formed thereon onto a disk having tracks which have address data record thereon.

Figure 5:
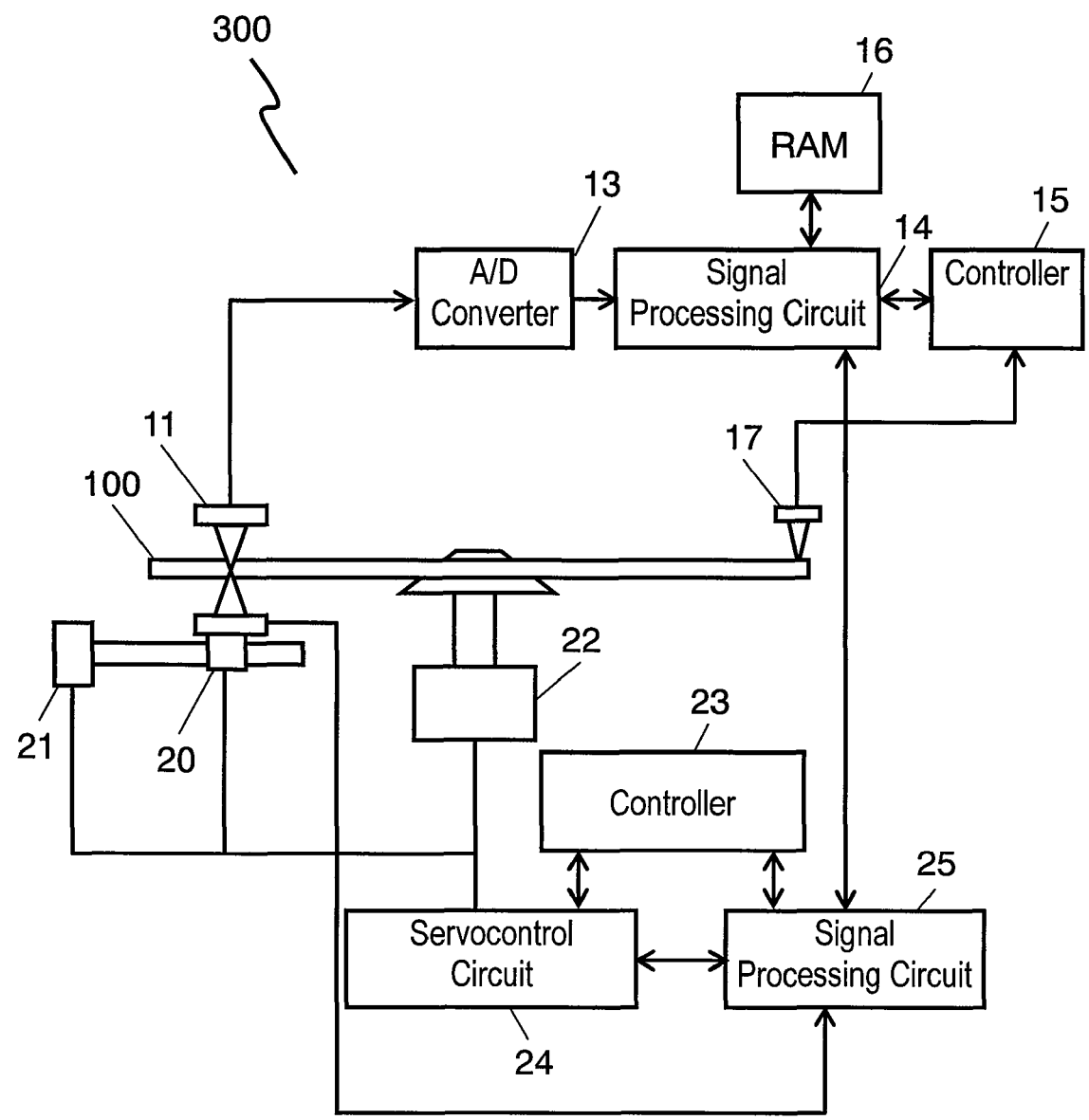
FIG. 5 is a block diagram of an analyzer according to Embodiment 1.

FIG. 5 is a block diagram of analyzer 300 in an analysis system according to Embodiment 1 using analyzing disk 1100. Analyzer 300 has a structure of a conventional optical disc drive. More specifically, analyzer 300 includes optical pickup 20 for illuminating disk 100 with laser, traverse motor 21 for moving optical pickup 20, driving unit 22, such as a spindle motor, for rotating disk 100, controller 23 for controlling these components, servocontrol circuit 24, and signal processing circuit 25 for converting a signal from optical pickup 20 to data. Photodetector 11 detects laser emitted from optical pickup 20 and transmitted through disk 100. A signal corresponding to the detected laser is converted to digital data by analog/digital (A/D) converter 13. The digital data is processed by signal processing circuit 14 and is stored in RAM 16. Controller 15 controls signal processing circuit 14 and RAM 16. Photosensor 17 detects trigger patterns 106 and 107 provided on disk 100. Optical pickup 20 for illuminating disk 100 with the laser and photodetector 11 for detecting the light from disk 100 provide an optical unit.

A method of analyzing a plasma component of blood as the test sample with analyzing disk 100 and analyzer 300 will be described.

Figure 2A:
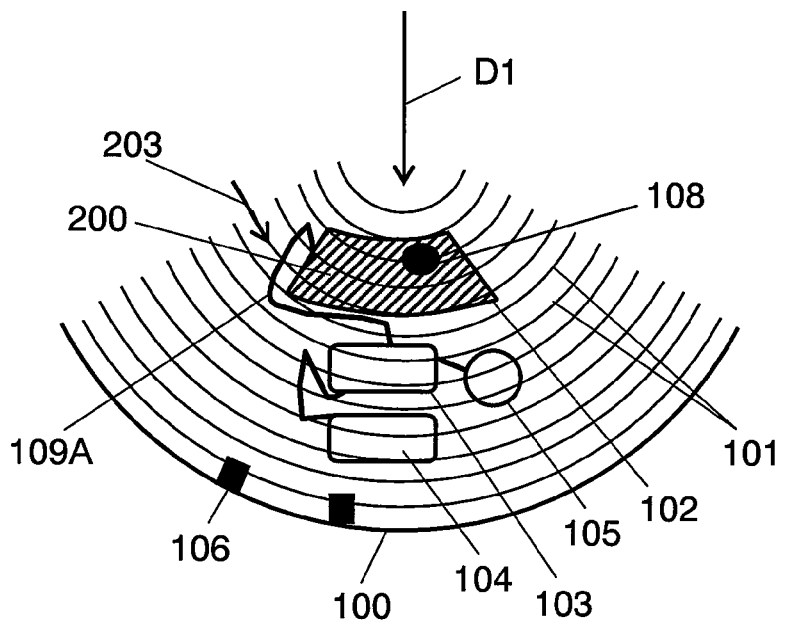
FIG. 2A is an enlarged top view of the analyzing disk according to Embodiment 1 of the invention.

FIG. 2A is an enlarged top view of analyzing disk 100 according to Embodiment 1. First, blood 200 is input through inlet 108 of analyzing disk 100 to fill centrifuge chamber 102. Then, disk 100 is inserted into analyzer 300. Analyzer 300 executes spin-up processes executed in a conventional optical disc drive as to prepare for tracing track 101 provided on analyzing disk 100.

After that, analyzing disk 100 rotates at a predetermined rotation speed for a predetermined time. After analyzing disk 100 rotates for the predetermined time, optical pickup 20 of analyzer 300 moves in radial direction D1 of analyzing disk 100 to start tracing track 101 at centrifuge chamber 102 in direction 203.

Photodetector 11 receives light emitted from optical pickup 20 and passing through disk 100 to output a signal corresponding to the light. While track 101 is traced, the signal output from photodetector 11 for a predetermined time after trigger pattern 106 is detected by photosensor 17 is converted to digital data by A/D converter 13, and the data is stored in RAM 16. Thus, the data from centrifuge chamber 102 is captured every time analyzing disk 100 rotates. The position of a portion of analyzing disk 100 from which the stored data is captured is determined by address data included in track 101. The position is stored in RAM 16 together with the data of the light detected by photodetector 11.

Figure 2B:
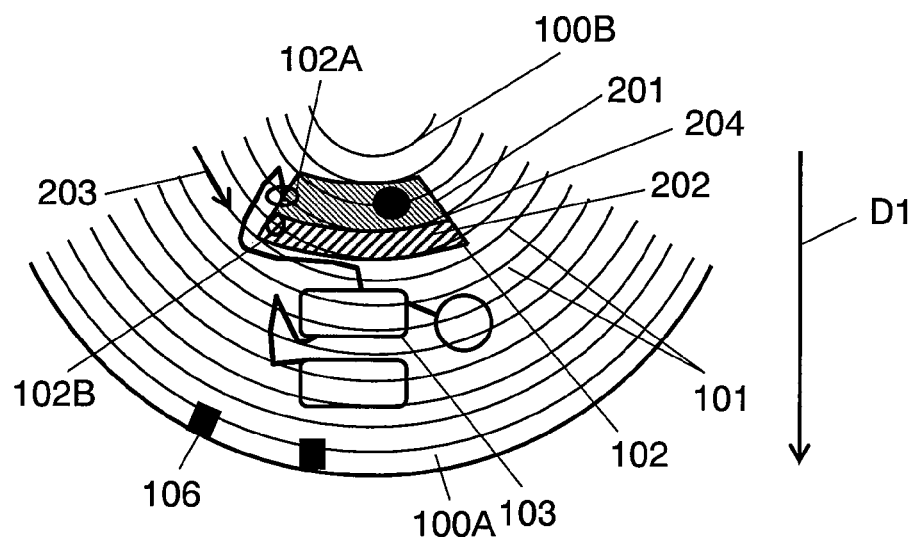
FIG. 2B is an enlarged top view of the analyzing disk according to Embodiment 1.

FIG. 2B is an enlarged top view of analyzing disk 100 according to Embodiment 1. Analyzing disk 100 rotates at the predetermined rotation speed for the predetermined time, and blood plasma component 201 and blood cell component 202 are separated from each other in centrifuge chamber 102 while disk 100 rotates. In this state, track 101 where centrifuge chamber 102 is positioned is traced as described above to acquire the address data and the data obtained by photodetector 11.

The amount of the light transmitting through centrifuge chamber 102 changes depending on presence or absence of the blood cell component. Thus, the data obtained by photodetector 11 clearly changes according to respective positions where blood plasma component 201 and blood cell component 202 exist, respectively. Controller 15 determines a position corresponding to the address data of this position where the data clearly changes as boundary 204 between blood plasma component 201 and blood cell component 202. It is determined based on boundary 204, as to judge the quality of the centrifugation.

In order to detect boundary 204, track 101 where centrifuge chamber 102 is positioned may be traced continuously. Alternatively, the analyzer may trace track 101 where centrifuge chamber 102 is positioned with a track jump partially, thereby detecting boundary 204 between blood plasma component 201 and blood cell component 202 efficiently.

In analyzing disk 100, a range in the radial direction of disk 100 within which boundary 204 between blood plasma component 201 and blood cell component 202 is positioned is previously stored as a predetermined reference range. Controller 15 can judge that the centrifugation has been normally executed if boundary 204 exists in the predetermined reference range. Controller 15 can judge that the centrifugation is inadequately or abnormally executed. The reference range may be recorded on track 101 of analyzing disk 100 as address data corresponding to the reference range.

The reference range is determined as follows. If the centrifugation ends when blood cell component 202 is positioned near point 102A where centrifuge chamber 102 is connected to capillary tube 109A, then, blood cell component 202 may be transferred to measuring chamber 103. Boundary 204 between blood plasma component 201 and blood cell component 202 is positioned closer to outer circumference 100A of disk 100 than to point 102A in radial direction D1 of analyzing disk 100.

As shown in FIG. 2B, a region closer to outer circumference 100A than to point 102A is determined as the reference range, and is stored as address data recorded on track 101. Photodetector 11 scans near point 102B closer to outer circumference 100A than to boundary 204 changes from data corresponding to light passing through blood plasma component 201 to data corresponding to light through blood cell component 202. Controller 15 judges that point 102B is boundary 204 between blood plasma component 201 and blood cell component 202, and detects that boundary 204 is located within the reference range, thus determining that the centrifugation has been executed appropriately.

Figure 3A:
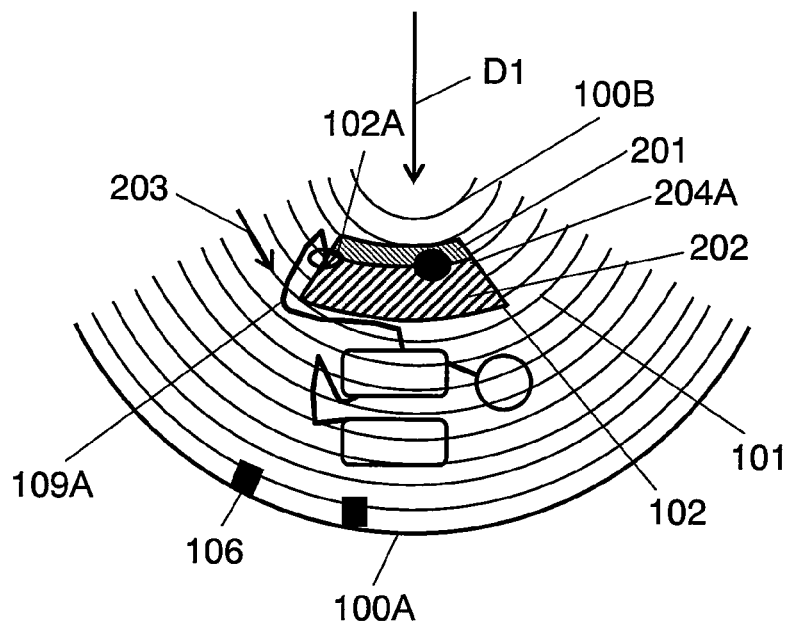
FIG. 3A is an enlarged top view of the analyzing disk according to Embodiment 1.
Figure 3B:
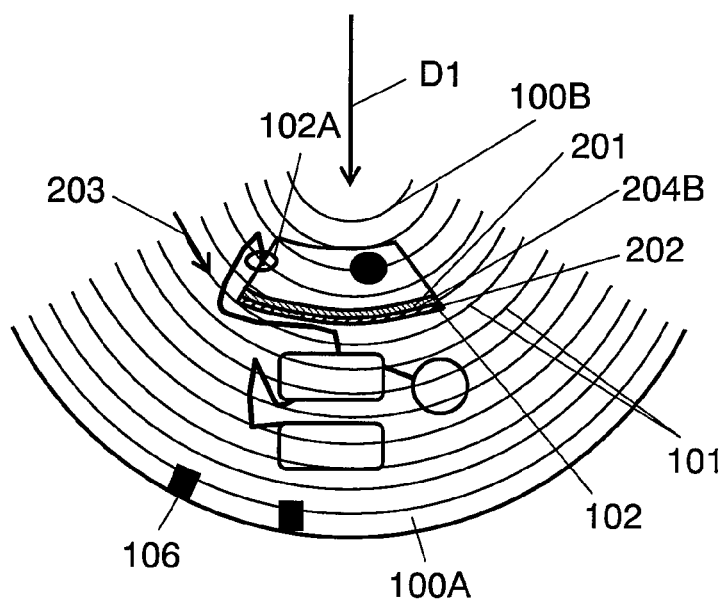
FIG. 3B is an enlarged top view of the analyzing disk according to Embodiment 1.

A way of judging whether or not the centrifugation under various statuses is executed appropriately will be explained. FIGS. 3A and 3B are enlarged top views of analyzing disk 100. In FIG. 3A, blood plasma component 201 and blood cell component 202 are not well separated even after being centrifuged for the predetermined time in the case that the blood is hardly separated. Boundary 204A between blood plasma component 201 and blood cell component 202 detected at this moment is closer to inner circumference 100B in radial direction D1 of analyzing disk 100 than to point 102A where centrifuge chamber 102 is connected to capillary tube 109A. That is, boundary 204A is out of the reference region, and controller 15 judges that the centrifugation is not sufficiently executed. In this case, controller 15 extends the time for executing the centrifugation or changes the rotation speed for the centrifugation, and then, monitors the status of the centrifugation again.

In FIG. 3B, an extremely small amount of blood cell component 202 is input into centrifuge chamber 102. This status appears if blood 200 flows out from centrifuge chamber 102 during the centrifugation, or if a small amount of blood 200 is input into centrifuge chamber 102. In this case, boundary 204B between blood plasma component 201 and blood cell component 202 is closer to outer circumference 100A than to point 102A. However, data obtained at point 102A by photodetector 11 is different from data corresponding to blood plasma component 201. Boundary 204B is thus out of the predetermined range, and hence, controller 15 judges that the centrifugation is executed inappropriately. This case does not provide an appropriate analysis result, and accordingly, controller 15 quits the analysis when judging that the centrifugation is executed inappropriately.

Figure 4:
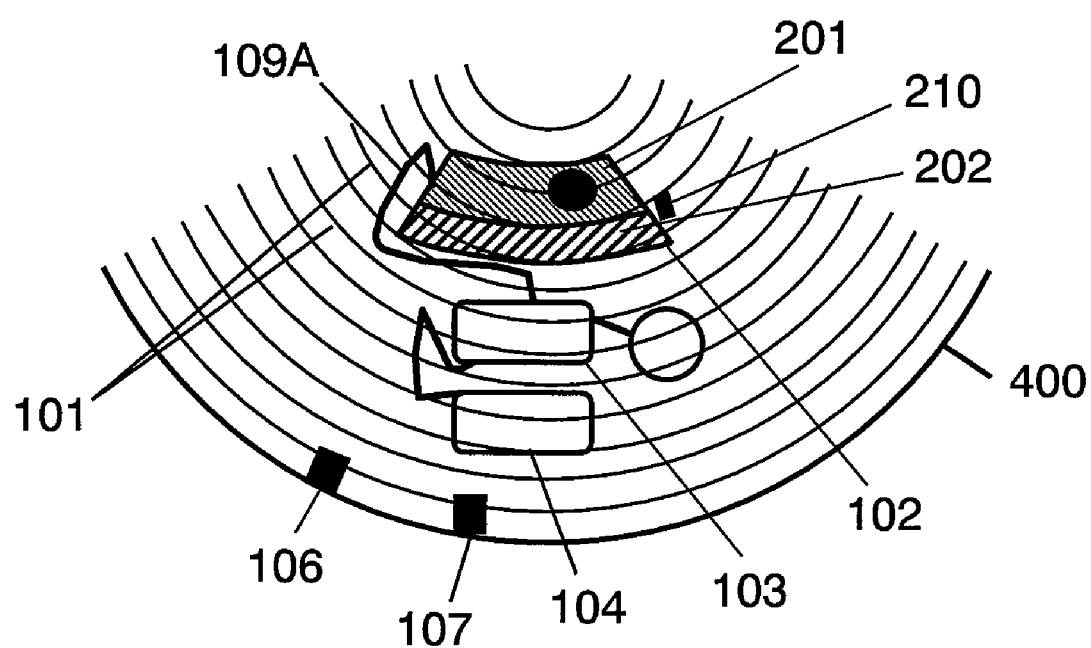
FIG. 4 is an enlarged top view of the analyzing disk according to Embodiment 1.

FIG. 4 is an enlarged top view of another analyzing disk 400 according to Embodiment 1. Data indicating the predetermined reference range is recorded as address data on track 101 of analyzing disk 400, and alternately, may be recorded as address data of marking 210 formed by printing or the like on analyzing disk 400. Trigger pattern 106 indicating the position of centrifuge chamber 102 is detected by photosensor 17. If photodetector 11 detects marking 210 within a predetermined after this detection, controller 15 can judge data obtained from photodetector 11 during the predetermined time as data within the predetermined reference range. Then, controller 15 judges, based on the obtained data, whether or not boundary 204 between blood plasma component 201 and blood cell component 202 exists, and checks the status the centrifugation.

When the centrifugation is completed, analyzing disk 400 is stopped rotating. When the rotation is stopped, the blood plasma to be tested which is separated in centrifuge chamber 102 and which is positioned at the inner circumference side of the disk is transferred to measuring chamber 103 through capillary tube 109A due to capillarity, and is collected. Then, analyzing disk 400 rotates again at a predetermined rotation speed for a predetermined time in order to measure the collected blood plasma component collected, and then, analyzing disk 400 is stopped rotating. When the rotation is stopped, the blood plasma component to be tested is transferred from measuring chamber 103 to analysis chamber 104 due to capillarity, and reacts with a reagent stored in analysis chamber 104.

When these processes are completed, optical pickup 20 moves to a radial position where analysis chamber 104 is located, and disk 400 rotates. Then, optical pickup 20 starts tracing track 101 of analyzing disk 400 at the position. Subsequently, trigger pattern 107 provided on analyzing disk 400 is detected by photosensor 17. Light transmitting from optical pickup 20 through analysis chamber 104 is detected by photodetector 11 for a predetermined time after trigger pattern 107 is detected by photosensor 17. A signal corresponding to the detected light is converted to digital data by A/D converter 13, and then the data is stored in RAM 16. The stored data allows the level of substance, such as cholesterol and glucose, in the blood plasma component as the test sample to be monitored, thus providing the analysis result.

When the centrifuging is executed in centrifuge chamber 102, controller 15 can judge, based on the position of boundary 204, whether or not the amount of blood plasma in blood 200 input into analysis chamber 104 exceeds a predetermined amount.

In analyzer 300 according to Embodiment 1, controller 15 thus monitors the status of the centrifugation to judge whether or not the centrifugation is executed appropriately, thereby preventing the component to be tested from being collected in measuring chamber 103 inappropriately, and preventing a component other than the component to be tested from being transferred to measuring chamber 103.

Controller 15 monitors the status of the centrifugation periodically by certain intervals, and thereby quits the centrifugation when boundary 204 between blood plasma component 201 and blood cell component 202 enters within the predetermined reference range, not when the centrifugation is continued to execute at a predetermined rotation speed for a predetermined time, thus shortening the time for the centrifugation.

The amount of blood 200 input into centrifuge chamber 102 may be predetermined, and then, the centrifugation status and boundary 204 may be detected. This operation enables respective volumes of blood plasma component 201 and blood cell component 202 to be calculated, thus enabling the hematocrit of blood 200 to be measured.

Analyzer 300 detects boundary 204 between blood plasma component 201 and blood cell component 202 in blood 200 based on the light transmitting through centrifuge chamber 102. Analyzer 300 may be detect boundary 204 based on light emitted from optical pickup 20 and reflected from centrifuge chamber 102.

According to Embodiment 1, the blood is employed as the test sample. Analyzer 300 and analyzing disks 100 and 400 according to Embodiment 1 may be used for other liquids, such as the pollution level of water, to be analyzed by the centrifugation as well.

Exemplary Embodiment 2

Figure 6:
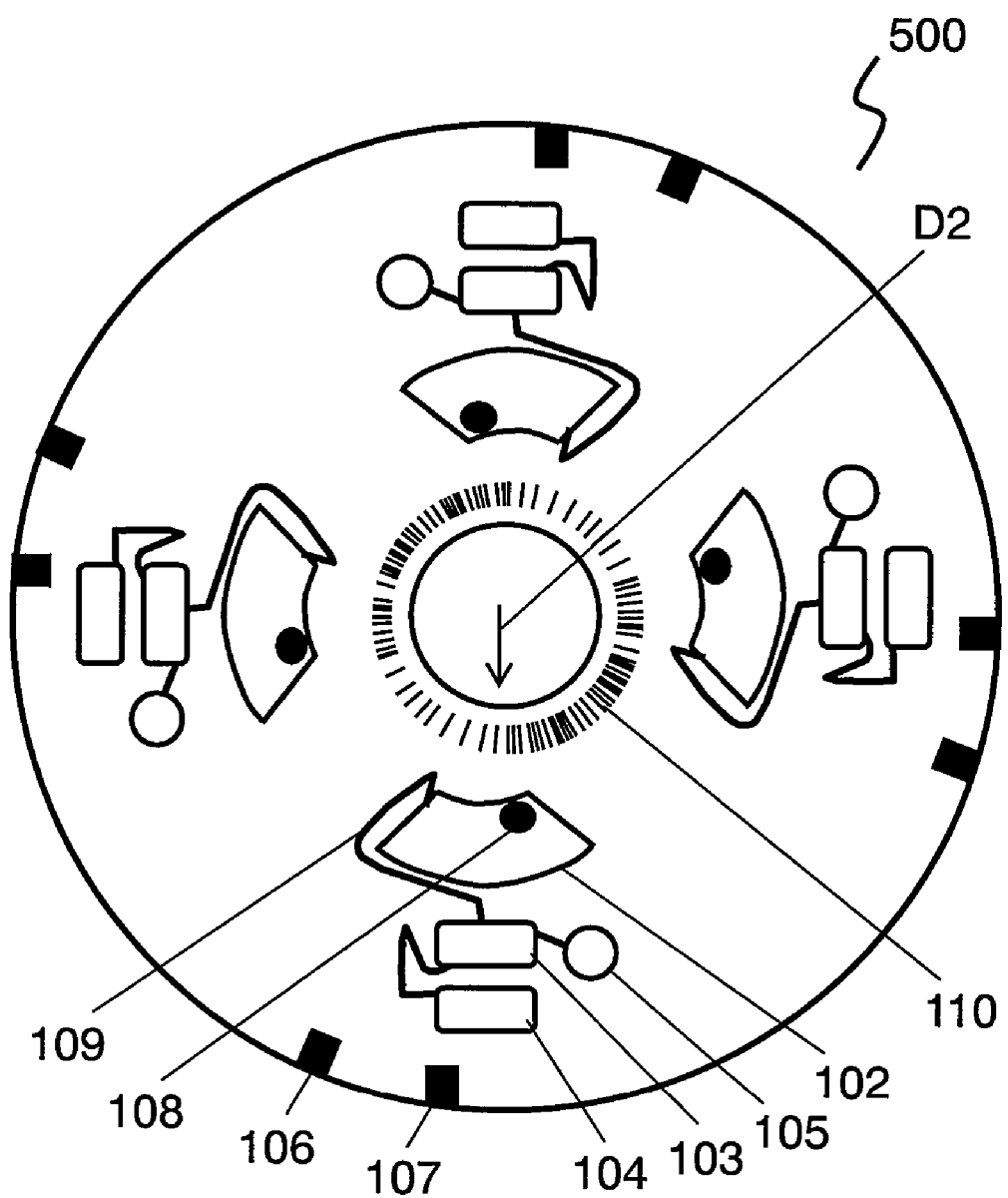
FIG. 6 is a top view of an analyzing disk according to Exemplary Embodiment 2 of the invention.
Figure 7:
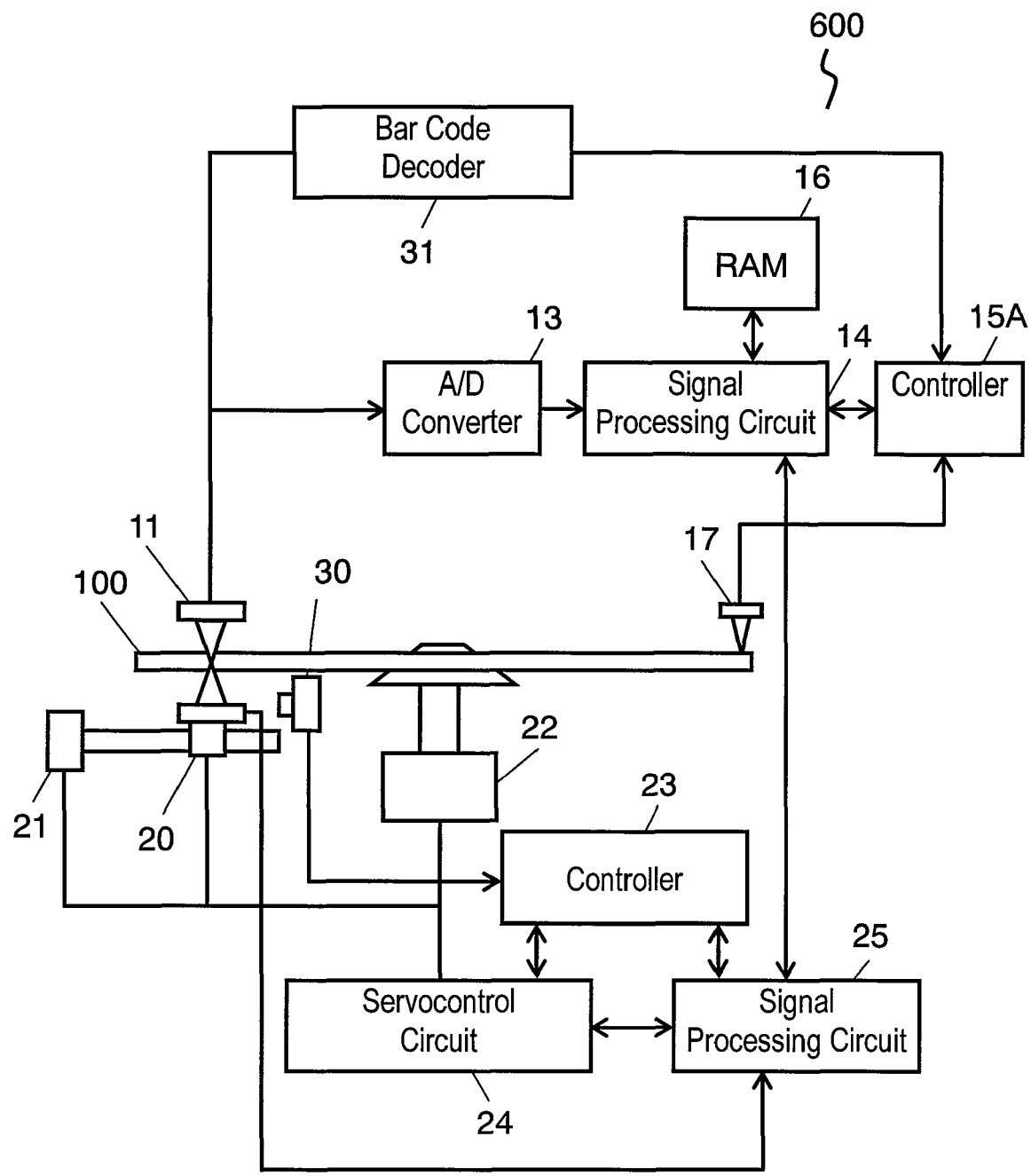
FIG. 7 is a block diagram of an analyzer according to Embodiment 2.
Figure 8:
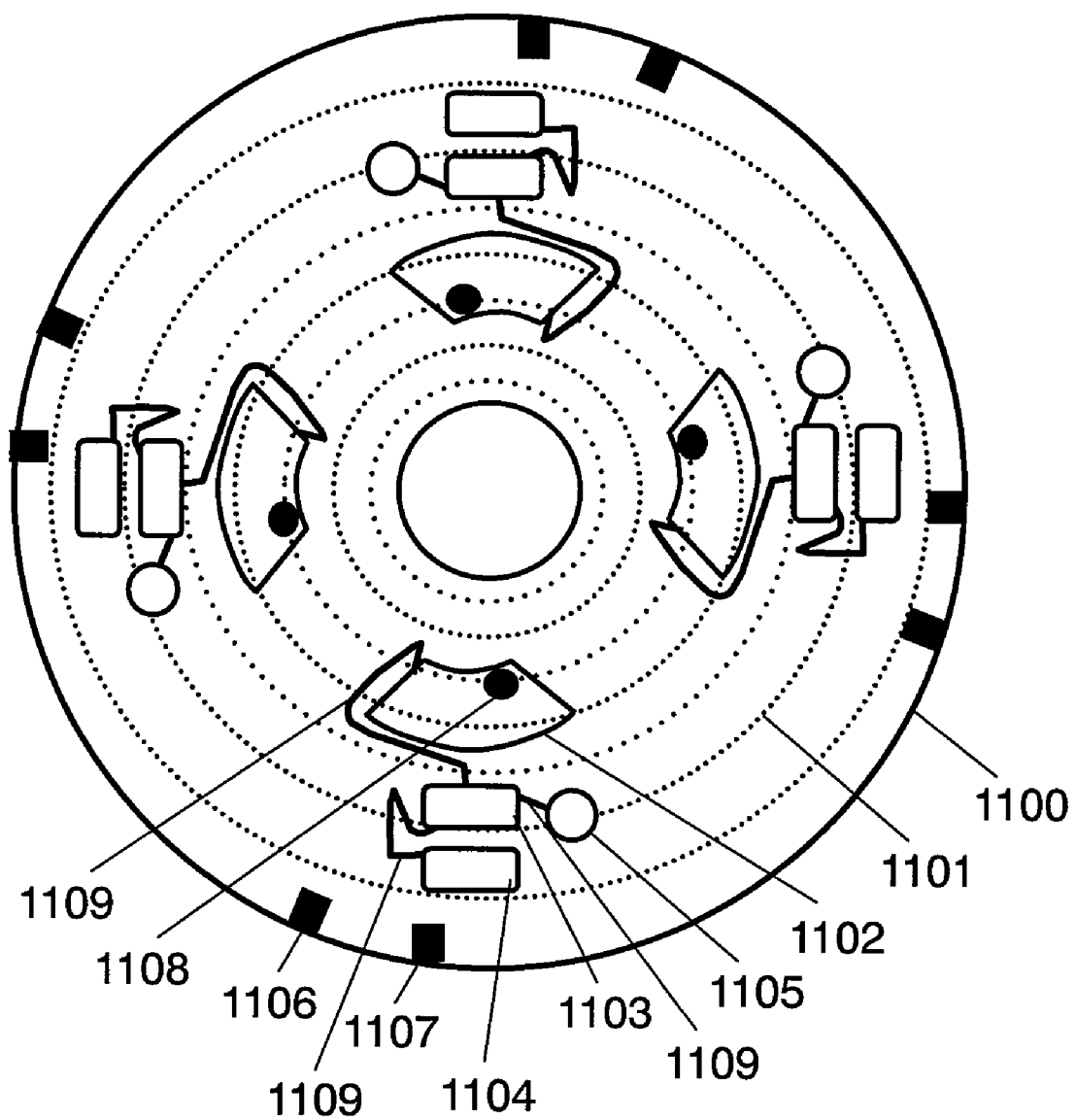
FIG. 8 is a top view of a conventional analyzing disk.
Figure 9:
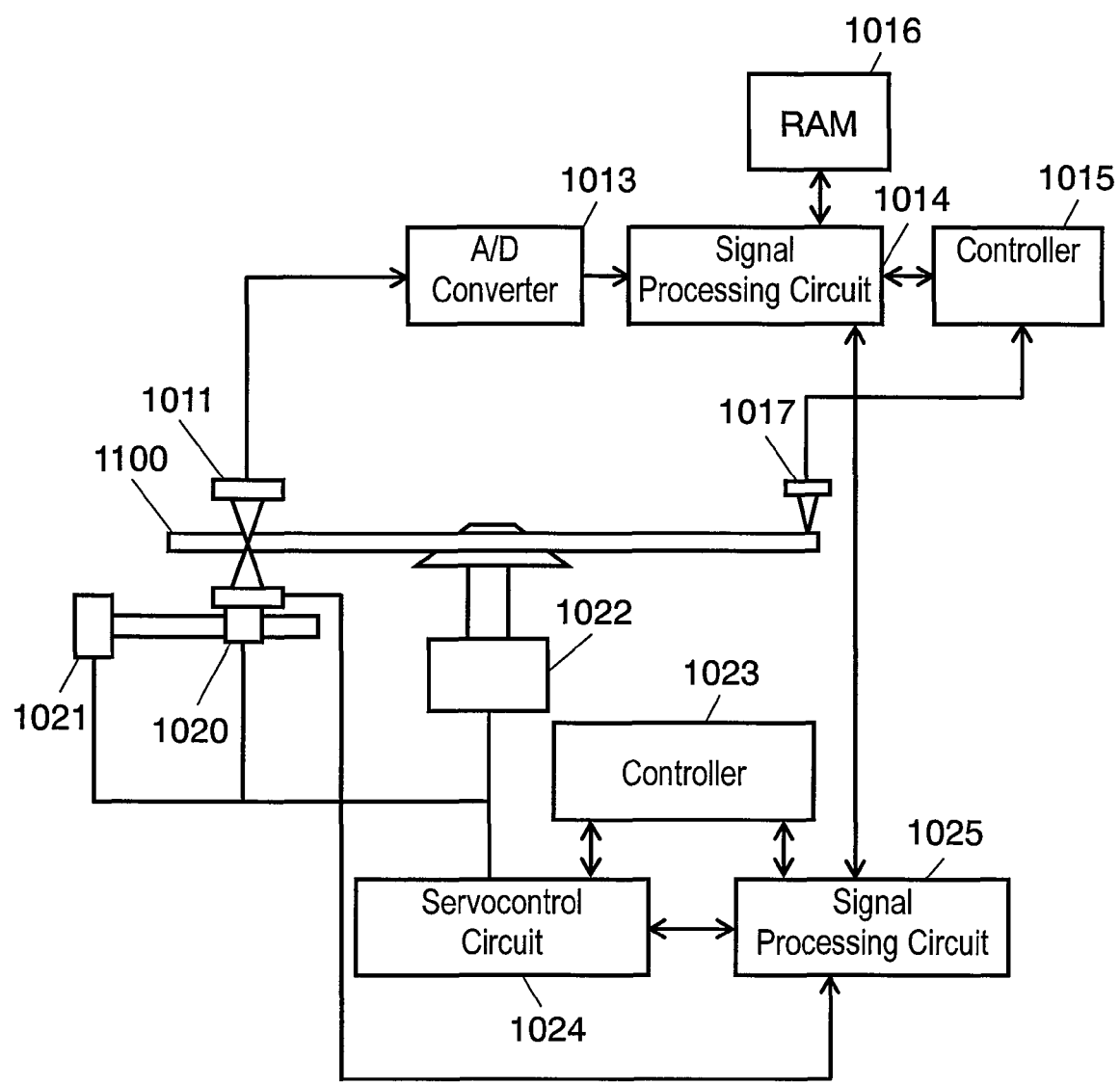
FIG. 9 is a block diagram of a conventional analyzer.

FIG. 6 is a top view of analyzing disk 500 according to Exemplary Embodiment 2. FIG. 7 is a block diagram of analyzer 600 according to Embodiment 2. Analyzing disk 500 has bar code 110 provided thereon instead of track 101 of disk 100 according to Embodiment 1 shown in FIG. 1. Analyzer 600 includes controller 15A having functions different from those of controller 15 of analyzer 300 according to Embodiment 1 shown in FIG. 5, further includes position-detecting switch 30 and bar code decoder 31. The same components as those of Embodiment 1 are denoted by the same reference numerals, and their description is omitted.

Bar code 110 records data to function as a reference required to check whether or not the centrifugation in centrifuge chamber 102 is executed appropriately. When optical pickup 20 moves to a position of centrifuge chamber 102 along radial direction D2 of disk 500, optical pickup 20 moves with reference to position-detecting switch 30 as a reference position, and traces disk 500 while further moving by a predetermined distance from the position to which optical pickup 20 previously moves.

First, analyzing disk 500 including centrifuge chamber 102 having blood input therein is inserted into analyzer 600, and then, rotates. While analyzing disk 500 rotates, optical pickup 20 moves to bar code 110 arranged at a specific position on analyzing disk 500, and bar code decoder 31 converts a signal detected by photodetector 11 into data to obtain data recorded in bar code 110. A part of the obtained data indicates the position of centrifuge chamber 102 provided on analyzing disk 500 and a predetermined reference range for the boundary between a plasma component and a cell component in order to judge whether or not the centrifugation is executed appropriately.

The position of centrifuge chamber 102 is determined by the distance from position-detecting switch 30, and optical pickup 20 moves to centrifuge chamber 102 based on this position. After moving, optical pickup 20 traces a region where centrifuge chamber 102 is provided while moving by a predetermined interval per one rotation of analyzing disk 500.

Similarly to Embodiment 1, when photosensor 17 detects trigger pattern 106 on analyzing disk 500 while tracing, a signal detected by photodetector 11 for a predetermined time is converted into digital data by A/D converter 13, and then the data is stored in RAM 16. The data from centrifuge chamber 102 is thus captured every time analyzing disk 500 rotates. The position of analyzing disk 500 from which the stored data has been captured is detected based on the distance by which optical pickup 20 moves from position-detecting switch 30. This distance and the data obtained by photodetector 11 are stored in RAM 16. Traverse motor 21 for moving optical pickup 20 may preferably be a motor, such as a stepping motor, that moves the pickup by a specified distance.

Analyzing disk 500 and analyzer 600, similarly to disk 100 and analyzer 300 according to Embodiment 1, monitor the status of the centrifugation, detect the boundary between the blood plasma component and the cell component, and determine the reference range within which the boundary to exist.

INDUSTRIAL APPLICABILITY

An analysis system according to the present invention monitors the status of separation in centrifugation, thus analyzing a sample accurately.

The invention claimed is:

1. An analysis system comprising:
   an analyzing disk including:
   a first chamber into which a test sample is input, the test sample including a first component and a second component;
   a second chamber into which the first component is input, for analyzing the first component; and
   a capillary tube for connecting the first chamber with the second chamber; and
   an analyzer including
   a driving unit for rotating the analyzing disk so as to centrifuge the first component and the second component of the test sample from each other in the first chamber;
   an optical unit movable in a radial direction of the analyzing disk, the optical unit illuminating light to the analyzing disk and detecting light from the test sample in the first chamber; and
   a controller for detecting, based on the light from the optical unit, a boundary between the first component and the second component centrifuged in the first chamber,
   wherein the controller judges whether or not the boundary is located in a predetermined range in the radial direction of the analyzing disk, and
   the controller judges whether or not an amount of the first component input into the second chamber reaches a predetermined amount based on a position of the boundary.

2. The analysis system of claim 1, wherein
   the controller is operable to judge whether or not the boundary is located in the predetermined range in the radial direction of the analyzing disk while the driving unit rotates the analyzing disk.

3. The analysis system of claim 1, wherein
   the analyzing disk further includes a track having address data indicating the range,
   the optical unit detects the track, and
   the controller determines the range based on the detected track.

4. The analysis system of claim 1, wherein
   the analyzing disk further including a marking indicating the range,
   the optical unit detects the marking, and
   the controller determines the range based on the detected marking.

5. The analysis system of claim 1, wherein
   the analyzing disk further including a bar code indicating the range,
   the optical unit reads the bar code, and
   the controller determines the range based on the read bar code.

6. The analysis system of claim 1, wherein the controller is operable to stop rotation of the analyzing disk when the controller judges that the boundary exists within the range, while the driving unit rotates the analyzing disk.

7. An analyzer arranged to have an analyzing disk input thereto, the analyzing disk having a first chamber and a second chamber, the first chamber being arranged to have a test sample input therein, the test sample including a first component and a second component, a second chamber into which the first component is input, for analyzing the first component, and a capillary tube that connects the first chamber with the second chamber, said analyzer comprising:
   a driving unit for rotating the analyzing disk so as to centrifuge the first component and the second component of the test sample from each other in the first chamber;
   an optical unit movable in a radial direction of the analyzing disk, the optical unit illuminating light to the analyzing disk and detecting light from the test sample in the first chamber; and
   a controller detecting, based on the light from the optical unit, a boundary between the first component and the second component centrifuged in the first chamber,
   wherein the controller judges whether or not the boundary is located within a predetermined range in the radial direction of the analyzing disk, and
   the controller judges whether or not an amount of the first component input into the second chamber reaches a predetermined amount based on a position of the boundary.

8. The analyzer of claim 7, wherein the controller is operable to judge whether or not the boundary is located within the predetermined range in the radial direction of the analyzing disk, while the driving unit rotates the analyzing disk.

9. The analyzer of claim 7, wherein
   the analyzing disk further includes a track having address data indicating the range,
   the optical unit detects the track, and
   the controller determines the range based on the detected track.

10. The analyzer of claim 7, wherein the analyzing disk further includes a marking indicating the range,
    the optical unit detects the marking, and
    the controller determines the range based on the detected marking.

11. The analyzer of claim 7, wherein
    the analyzing disk further includes a bar code indicating the range,
    the optical unit reads the bar code, and
    the controller determines the range based on the read bar code.

12. The analyzer of claim 7, wherein the controller is operable to stop rotation of the analyzing disk when the controller judges that the boundary exists in the range, while the driving unit rotates the analyzing disk.

* * * * *